United States Patent
Greaves

(10) Patent No.: US 7,220,286 B2
(45) Date of Patent: May 22, 2007

(54) CATIONIC DIRECT TRIAZO DYES, DYE COMPOSITION COMPRISING THEM AND PROCESS FOR DYEING KERATIN FIBRES USING IT

(75) Inventor: Andrew Greaves, Montevrain (FR)

(73) Assignee: L'Oreal SA, Paris (FR)

( * ) Notice: Subject to any disclaimer, the term of this patent is extended or adjusted under 35 U.S.C. 154(b) by 230 days.

(21) Appl. No.: 11/033,998

(22) Filed: Jan. 13, 2005

(65) Prior Publication Data
US 2006/0016022 A1    Jan. 26, 2006

Related U.S. Application Data

(60) Provisional application No. 60/566,092, filed on Apr. 29, 2004.

(30) Foreign Application Priority Data
Jan. 13, 2004    (FR) .................... 04 50073

(51) Int. Cl.
*A61K 7/13*    (2006.01)
(52) U.S. Cl. .................. 8/405; 8/406; 8/408; 8/437; 8/565; 8/566; 8/567; 8/568; 8/570; 8/571; 8/572; 8/573; 8/574; 8/654; 8/655; 546/184; 548/318.1; 548/400
(58) Field of Classification Search .............. 8/405, 8/406, 408, 437, 565, 566, 567, 568, 570, 8/571, 572, 573, 574, 654, 655; 546/184; 548/318.1, 400
See application file for complete search history.

(56) References Cited

U.S. PATENT DOCUMENTS

| 5,708,151 | A | * | 1/1998 | Mockli | ........................ | 534/608 |
|---|---|---|---|---|---|---|
| 5,919,273 | A | | 7/1999 | Rondeau et al. | | |

FOREIGN PATENT DOCUMENTS

| EP | 0 714 954 B1 | 6/1996 |
|---|---|---|
| EP | 0 850 636 B1 | 7/1998 |
| WO | WO 02/100834 A1 | 12/2002 |

OTHER PUBLICATIONS

STIC Search Report dated, no date.*

\* cited by examiner

*Primary Examiner*—Eisa Elhilo
(74) *Attorney, Agent, or Firm*—Finnegan, Henderson, Farabow, Garrett & Dunner, LLP

(57) ABSTRACT

The present invention relates to cationic direct dyes of formula (I) below:

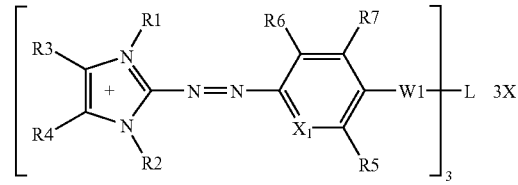

in which $W_1$ represents —$NR_8$— or —O—; $X_1$ represents N; $CR_9$; $R_1$ and $R_2$, which may be identical or different, represent a hydrocarbon chain; $R_3$ and $R_4$, which may be identical or different, represent a hydrogen atom, a halogen atom, a nitro group, a cyano group or a hydrocarbon chain; $R_5$, $R_6$, $R_7$, $R_8$ and $R_9$, which may be identical or different, represent a hydrogen atom or a hydrocarbon chain; L represents a specific bridging group and X represents a cosmetically acceptable organic or mineral anion.

It likewise relates to a dye composition comprising, in a medium suitable for dyeing human keratin fibers, such a dye, a process using it, and also a multicompartment device.

37 Claims, No Drawings

CATIONIC DIRECT TRIAZO DYES, DYE COMPOSITION COMPRISING THEM AND PROCESS FOR DYEING KERATIN FIBRES USING IT

The present invention relates to specific cationic direct triazo dyes, to a dye composition comprising them, and also to a process for dyeing keratin fibers using it.

The invention relates to the field of the dyeing of human keratin fibers, in particular of the hair. More particularly, it relates to the colorations obtained by means of dye compositions containing at least one direct dye.

Direct dyes are coloured and colouring substances which have a certain affinity with human keratin fibers.

Generally, these direct dyes are chosen from nitrobenzene dyes, azo, azomethine, methine, anthraquinone, naphthoquinone, benzoquinone, phenothiazine, indigoid, xanthene, phenanthridine and phthalocyanin dyes, from those derived from triarylmethane, and also natural dyes, alone or as mixtures.

Among the dyes that have the advantage of resulting in very chromatic colours, mention may more particularly be made of azo-type dyes comprising at least one heterocycle, such as, for example, the direct dye Basic Red 22 which makes it possible to obtain orangey-red colours.

The disadvantage of these direct dyes lies in the fact that the resistance to shampooing of the colours obtained is still judged to be too poor.

One of the aims of the present invention is therefore to provide direct dyes for obtaining colours with improved resistance, in particular with respect to shampooing, without decreasing the properties of uptake of the dye onto the fibre or degrading the selectivity characteristics of the dye.

Thus, a subject of the present invention is cationic direct dyes of formula (I) below:

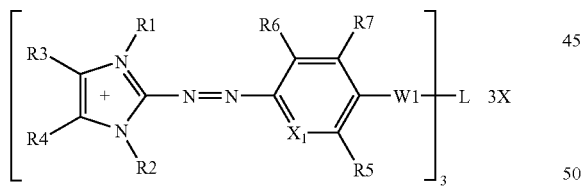

and their tautomeric forms, in which formula
$W_1$ represents —$NR_8$— or —O—;
$X_1$ represents N; $CR_9$;
$R_1$ and $R_2$, which may be identical or different, represent a hydrocarbon chain;
$R_3$ and $R_4$, which may be identical or different, represent a hydrogen atom, a halogen atom, a nitro group, a cyano group or a hydrocarbon chain;
$R_5$, $R_6$, $R_7$, $R_8$ and $R_9$, which may be identical or different, represent a hydrogen atom or a hydrocarbon chain;
L represents one of the groups below:

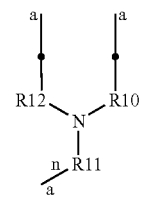

Formula (II)

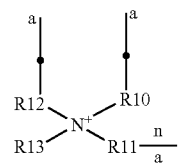

Formula (III)

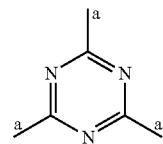

Formula (IV)

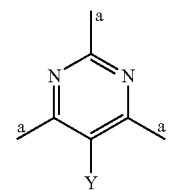

Formula (V)

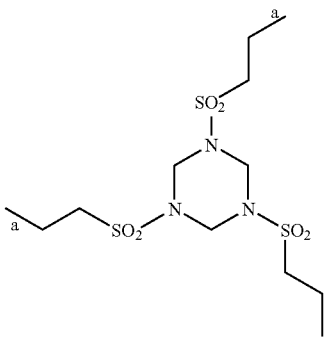

Formula (VI)

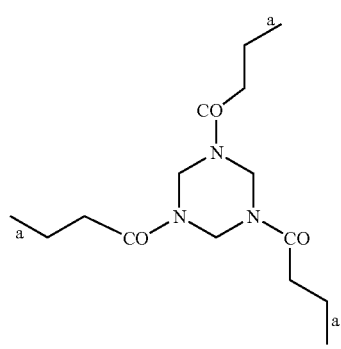

Formula (VII)

in which:
$R_{10}$, $R_{11}$, $R_{12}$ and $R_{13}$, which may be identical or different, represent a hydrocarbon chain;
Y represents a halogen atom, preferably fluorine or chlorine;

the bond a of formulae (II) to (VII) is connected to the group $W_1$ of formula (I);

X represents a cosmetically acceptable organic or mineral anion.

Similarly, a subject of the present invention is a dye composition comprising, in a medium suitable for dyeing human keratin fibers, at least one dye of formula (I) mentioned above.

The present invention also relates to a process for dyeing human keratin fibers, in which the following steps are carried out:
a) said fibers, dry or wet, are brought into contact with the dye composition according to the invention for a period of time sufficient to develop the coloration,
b) the fibers are optionally rinsed,
c) the fibers are optionally washed and rinsed,
d) the fibers are dried or are left to dry.

Finally, a subject of the invention is the dyes of formula (I) mentioned above.

However, other advantages and characteristics of the invention will emerge more clearly on reading the description and the examples which follow.

In the following text, when ranges are described as being between two values, these values are inclusive, unless otherwise indicated.

As previously indicated, the cationic direct dyes in accordance with the present invention are provided by means of the compounds of formula (I).

In the text, unless otherwise indicated, when reference is made to a hydrocarbon chain, the following is denoted:
a linear or branched, saturated or unsaturated $C_1$–$C_8$ hydrocarbon chain optionally interrupted with one or more hetero atoms such as oxygen, nitrogen or sulphur, and/or with one or more carbonyl or $SO_2$ groups, said chain comprising no hetero atom adjacent to one or more hetero atoms, nor a carbonyl or $SO_2$ group adjacent to one or more carbonyl and/or $SO_2$ groups;
and/or an aromatic $C_5$–$C_6$ hydrocarbon chain;
furthermore, the hydrocarbon chain is optionally substituted with one or more radicals chosen from a hydroxyl radical; a halogen atom, and preferably chlorine or fluorine; a $C_1$–$C_4$ alkoxy radical; a monohydroxyalkoxy radical in which the alkyl portion is a linear or branched, substituted or unsubstituted $C_1$–$C_4$ alkyl; a polyhydroxyalkoxy radical, in which the alkyl portion is a linear or branched, substituted or unsubstituted $C_2$–$C_4$ alkyl; an amino radical that is unsubstituted or substituted with one or more linear or branched, substituted or unsubstituted $C_1$–$C_4$ alkyl radicals that may be identical or different; a thiol radical; an alkylthio radical in which the alkyl portion is a linear or branched, substituted or unsubstituted $C_1$–$C_4$ alkyl; a carboxyl radical either in acid form or salified form (with an alkali metal or an ammonium that may or may not be substituted); an alkoxycarbonyl radical in which the alkyl portion is a linear or branched, substituted or unsubstituted $C_1$–$C_4$ alkyl; an alkylamide radical in which the alkyl portion is a linear or branched, substituted or unsubstituted $C_1$–$C_4$ alkyl; an alkylcarbamyl radical in which the alkyl portion is a linear or branched, substituted or unsubstituted $C_1$–$C_4$ alkyl; a nitro radical; a sulphonyl radical; an alkylsulphonyl radical in which the alkyl portion is a linear or branched, substituted or unsubstituted $C_1$–$C_4$ alkyl; a sulphonylamino radical or an alkylsulphonylamido radical in which the alkyl portion is a linear or branched, substituted or unsubstituted $C_1$–$C_4$ alkyl.

It should be noted that the alkyl radicals or the alkyl portions of the substituent radicals can themselves be substituted with one of the radicals listed above.

However, the alkyl radicals or the alkyl portions of these substituent radicals are preferably not substituted, or else are substituted with one or more radicals chosen from hydroxyl radicals; halogen atoms such as, for example, chlorine or fluorine; $C_1$–$C_4$ alkoxy radicals; monohydroxyalkoxy radicals in which the alkyl portion is a $C_1$–$C_4$ alkyl; amino radicals; amino radicals substituted with one or more $C_1$–$C_4$ alkyl radicals which may be identical or different.

More particularly, the radicals $R_1$ and $R_2$, which may be identical or different, represent a $C_1$–$C_8$ alkyl or $C_2$–$C_8$ alkenyl radical optionally carrying one or more of the following radicals: hydroxyl, amino, amino substituted with one or more $C_1$–$C_8$ alkyl radicals optionally carrying at least one hydroxyl radical; a $C_1$–$C_8$ alkoxy radical; a $C_6$-aryl ($C_1$–$C_4$) alkyl radical.

Particularly advantageously, the radicals $R_1$ and $R_2$, which may be identical or different, represent a $C_1$–$C_4$ alkyl radical or a benzyl radical.

The radicals $R_1$ and $R_2$, which may be identical or different, preferably represent a methyl or ethyl radical.

According to a particular embodiment, the radicals $R_3$ and $R_4$, which may be identical or different, represent a hydrogen atom; a halogen atom, preferably chlorine; a nitro group; a cyano group; a $C_1$–$C_8$ alkyl or $C_2$–$C_8$ alkenyl radical optionally carrying one or more of the following radicals: hydroxyl, amino, amino substituted with one or more $C_1$–$C_8$ alkyl radicals optionally carrying at least one hydroxyl radical; a $C_1$–$C_8$ alkoxy radical; a $C_1$–$C_8$ alkylthio radical; a sulphonylamino radical; a phenyl radical.

More advantageously, said radicals $R_3$ and $R_4$, which may be identical or different, represent a hydrogen atom; a chlorine atom; a $C_1$–$C_8$ alkyl or $C_2$–$C_8$ alkenyl radical optionally carrying one or more of the following radicals: hydroxyl, amino, amino substituted with one or more $C_1$–$C_8$ alkyl radicals optionally carrying at least one hydroxyl radical, a $C_1$–$C_8$ alkoxy radical; a phenyl radical.

Preferably, the radicals $R_3$ and $R_4$ represent a hydrogen atom, a chlorine atom or a phenyl radical.

As regards the radicals $R_5$, $R_6$, $R_7$, $R_8$ and $R_9$, which may be identical or different, they represent more particularly a hydrogen atom; a $C_1$–$C_8$ alkyl or $C_2$–$C_8$ alkenyl radical optionally carrying one or more of the following radicals: hydroxyl, amino, amino substituted with one or more $C_1$–$C_8$ alkyl radicals optionally carrying at least one hydroxyl radical; a $C_1$–$C_8$ alkoxy radical; a $C_1$–$C_8$ alkylthio radical; a sulfonylamino radical.

Advantageously, the radicals $R_5$, $R_6$, $R_7$, $R_8$ and $R_9$, which may be identical or different, represent a hydrogen atom, a $C_1$–$C_4$ alkyl radical optionally carrying one or more of the following radicals: hydroxyl, amino, amino substituted with one or more $C_1$–$C_8$ alkyl radicals optionally carrying at least one hydroxyl radical; a $C_1$–$C_4$ alkoxy radical.

Preferably, the radicals $R_5$, $R_6$, $R_7$, $R_8$ and $R_9$, which may be identical or different, represent a hydrogen atom or a $C_1$–$C_4$ alkyl radical.

In accordance with an even more preferred embodiment of the invention, the radicals $R_3$, $R_4$, $R_5$, $R_6$, $R_7$, $R_8$ and $R_9$ represent a hydrogen atom.

In the formulae (II) to (VII), the radicals $R_{10}$, $R_{11}$, $R_{12}$ and $R_{13}$, which may be identical or different, represent more particularly a hydrogen atom; a $C_1$–$C_8$ alkyl or $C_2$–$C_8$ alkenyl radical optionally carrying one or more of the following radicals: hydroxyl, amino, amino substituted with one or more $C_1$–$C_8$ alkyl radicals optionally carrying at least one hydroxyl radical; a $C_1$–$C_8$ alkoxy radical; a $C_1$–$C_8$ alkylthio radical; a sulphonylamino radical.

Said radicals $R_{10}$, $R_{11}$, $R_{12}$ and $R_{13}$, according to a preferred embodiment of the invention, which may be identical or different, represent a $C_1$–$C_4$ alkyl radical optionally carrying one or more of the following radicals: hydroxyl, amino, amino substituted with one or more $C_1$–$C_4$ alkyl radicals optionally carrying at least one hydroxyl radical; a $C_1$–$C_4$ alkoxy radical.

Even more preferably, the radicals $R_{10}$, $R_{11}$, $R_{12}$ and $R_{13}$, which may be identical or different, represent an ethyl, n-propyl or n-butyl radical.

In accordance with a particular embodiment of the invention, $X_1$ represents a divalent group $CR_9$, $R_9$ being defined above.

$R_9$ preferably represents a hydrogen atom.

Moreover, a particularly advantageous variant of the invention corresponds to a dye of formula (I) in which $W_1$ represents a divalent group $NR_8$, $R_8$ having the same definition as those given above.

More particularly, $R_8$ represents a $C_1$–$C_4$ alkyl radical, and preferably a hydrogen atom.

The direct dye of formula (I) also comprises a cosmetically acceptable anion that is organic or mineral in nature.

By way of example of anions that are mineral in nature, mention may in particular be made of halides, such as chlorides; hydroxides, sulphates; hydrogen sulphates.

By way of examples of anions that are organic in nature, suitable anions are, for instance, acetate; citrate; tartrate; alkyl sulphates for which the linear or branched alkyl portion is a $C_1$–$C_6$ alkyl, such as the methosulphate or ethosulphate ion; alkylsulphonates for which the linear or branched alkyl portion is a $C_1$–$C_6$ alkyl; arylsulphonates for which the aryl, preferably phenyl, portion is optionally substituted with one or more $C_1$–$C_4$ alkyl radicals.

A preferred embodiment of the invention consists of direct dyes of formula (I), chosen from the following compounds:

2-((E)-{4-[(3-{bis[3-({4-[(E)-(1,3-dimethyl-1H-imidazol-3-ium-2-yl)diazenyl]phenyl}amino)propyl]amino}propyl)amino]phenyl}diazenyl)-1,3-dimethyl-1H-imidazol-3-ium trichloride 2-{(E)-[4-({3-[bis[3-({4-[(E)-(1,3-dimethyl-1H-imidazol-3-ium-2-yl)diazenyl]phenyl}amino)propyl](methyl)ammonio]propyl}amino)phenyl]-diazenyl}-1,3-dimethyl-1H-imidazol-3-ium tetrachloride 2-((E)-{4-[{3-[bis{3-[{4-[(E)-(1,3-dimethyl-1H-imidazol-3-ium-2-yl)diazenyl]phenyl}(methyl)amino]propyl}(methyl)ammonio]propyl}(methyl)amino]phenyl}diazenyl)-1,3-dimethyl-1H-imidazol-3-ium tetrachloride 2-((E)-{4-[{3-[bis{3-[{4-[(E)-(1,3-diethyl-1H-imidazol-3-ium-2-yl)diazenyl]phenyl}(ethyl)amino]propyl}(ethyl)ammonio]propyl}(ethyl)amino]phenyl}diazenyl)-1,3-diethyl-1H-imidazol-3-ium tetrachloride 2-((E)-{4-[{3-[bis{3-[{4-((E)-(1,3-dimethyl-1H-imidazol-3-ium-2-yl)diazenyl]phenyl}(ethyl)amino]propyl}(ethyl)ammonio]propyl}(ethyl)amino]phenyl}diazenyl)-1,3-dimethyl-1H-imidazol-3-ium tetrachloride 2-((E)-{4-[(3-{3,5-bis[3-({4-[(E)-(1,3-dimethyl-1H-imidazol-3-ium-2-yl)diazenyl]phenyl}amino)propanoyl]-1,3,5-triazinan-1-yl}-3-oxopropyl]amino]phenyl}diazenyl)-1,3-dimethyl-1H-imidazol-3-ium trichloride 2-((E)-{4-[[3-(3,5-bis{3-[{4-[(E)-(1,3-dimethyl-1H-imidazol-3-ium-2-yl)diazenyl]phenyl}(ethyl)amino]propanoyl}-1,3,5-triazinan-1-yl)-3-oxopropyl](ethyl)amino]phenyl}diazenyl)-1,3-dimethyl-1H-imidazol-3-ium trichloride 2-{(E)-[4-({2-[(3,5-bis{[2-({4-[(E)-(1,3-dimethyl-1H-imidazol-3-ium-2-yl)diazenyl]phenyl}amino)ethyl]sulphonyl}-1,3,5-triazinan-1-yl)sulphonyl]ethyl}amino)phenyl]diazenyl}-1,3-dimethyl-1H-imidazol-3-ium trichloride 2-((E)-{4-[(2-{[3,5-bis({2-[{4-[(E)-(1,3-dimethyl-1H-imidazol-3-ium-2-yl)diazenyl]phenyl}(ethyl)amino]ethyl}sulphonyl)-1,3,5-triazinan-1-yl]sulphonyl}ethyl)(ethyl)amino]phenyl}diazenyl)-1,3-dimethyl-1H-imidazol-3-ium trichloride 2-[(E)-(4-{[4,6-bis({4-[(E)-(1,3-dimethyl-1H-imidazol-3-ium-2-yl)diazenyl]phenyl}amino)-1,3,5-triazin-2-yl]amino}phenyl)diazenyl]-1,3-dimethyl-1H-imidazol-3-ium trichloride 2-((E)-{4-[[4,6-bis[{4-[(E)-(1,3-dimethyl-1H-imidazol-3-ium-2-yl)diazenyl]phenyl}(methyl)amino]-1,3,5-triazin-2-yl}(methyl)amino]phenyl}diazenyl)-1,3-dimethyl-1H-imidazol-3-ium trichloride 2-[(E)-(4-{[5–Chloro-2,6-bis({4-[(E)-(1,3-dimethyl-1H-imidazol-3-ium-2-yl)diazenyl]phenyl}amino)pyrimidin-4-yl]amino}phenyl)diazenyl]-1,3-dimethyl-1H-imidazol-3-ium trichloride 2-((E)-{4-[[5–Chloro-2,6-bis[{4-[(E)-(1,3-dimethyl-1H-imidazol-3-ium-2-yl)diazenyl]phenyl}(methyl)amino]pyrimidin-4-yl](methyl)amino]-phenyl}diazenyl)-1,3-dimethyl-1H-imidazol-3-ium trichloride.

Of course, in the above list, the counterion can be changed and chosen from the cosmetically acceptable anions of organic or mineral nature listed previously.

These dyes can be synthesized conventionally, and reference may be made to the work Advanced Organic Chemistry, March, 4th Ed.

However, by way of example, one of the two pathways mentioned below may be implemented:

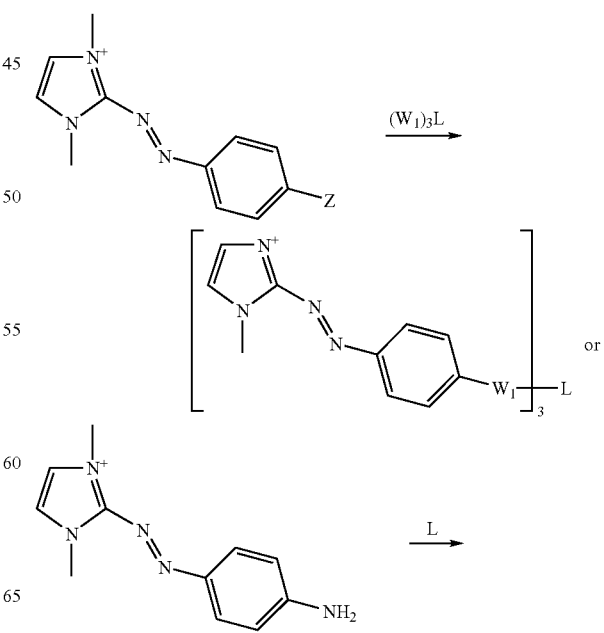

-continued

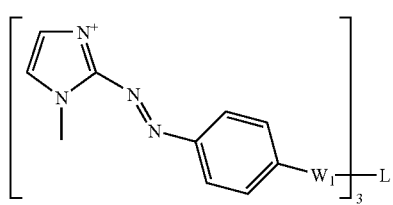

In these formulae, Z can represent a group of —OR type in which R is a linear or branched $C_1$–$C_4$ alkyl radical; a group of —$OSO_2R'$ type with R' representing a linear or branched $C_1$–$C_4$ alkyl radical, a $C_6$-aryl radical; a halogen atom.

The substitution reaction can be carried out entirely conventionally, and reference may be made to the work Advanced Organic Chemistry, March, 4th Ed., for further details on the operating conditions used.

To obtain compounds in which L represents a radical of formula (VI) or (VII), Michael reactions can, for example, be carried out.

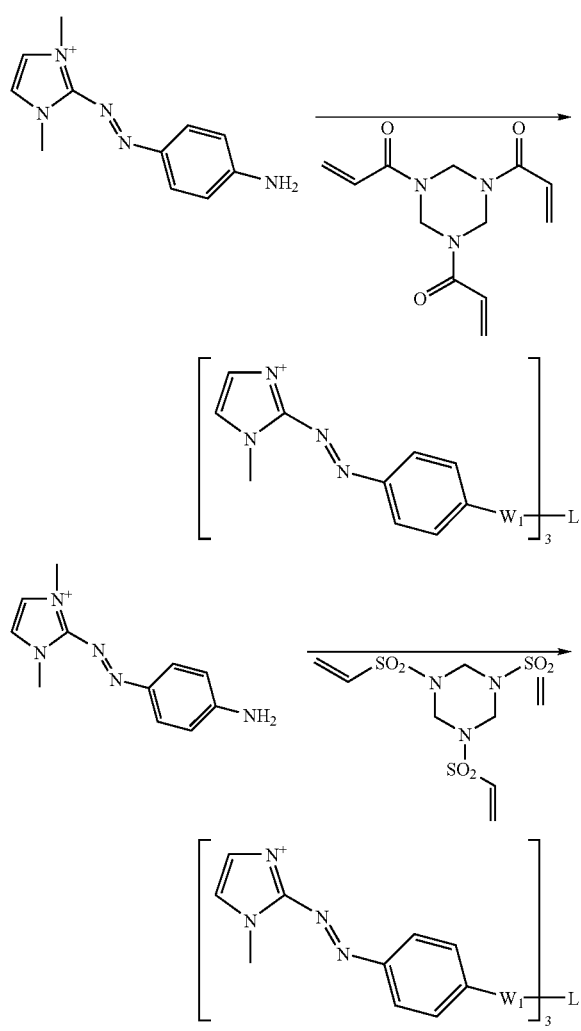

Conventional substitution reactions can be carried out in order to obtain compounds in which L represents a radical of formula (IV) or (V).

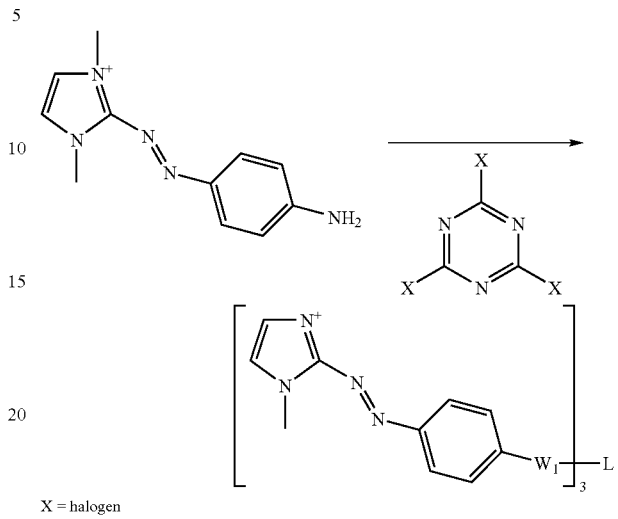

X = halogen

A subject of the present invention is a dye composition comprising, in a medium suitable for dyeing human keratin fibers in particular the hair, at least one cationic direct dye of formula (I), details of which have just been given.

More particularly, the content of dye of formula (I) is between 0.001 and 20% by weight relative to the weight of the dye composition, preferably between 0.01 and 10% by weight relative to the weight of the dye composition.

It should be noted that the composition can comprise at least one additional direct dye different from that which has just been described, at least one oxidation base and/or at least one coupler, or mixtures thereof.

As regards the additional direct dyes, cationic, anionic or nonionic species may be used.

Advantageously, they can be chosen from nitrobenzene dyes, and acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanin (such as in particular azacarbocyanin, diazacarbocyanin, diazahemicyanin, hemicyanin, tetraazacarbocyanin), diazine, diketopyrrolopyrrole, dioxazine, diphenylamine, diphenylmethane, dithiazine, flavanthrone, flavone, fluorindine, formazan, hydrazone, hydroxy ketone, indamine, indanthrone, indigoid, indophenol, indoaniline, isoindoline, isoindolinone, isoviolanthrone, lactone, methine, naphthalimide, naphthanilide, naphtholactam, naphthoquinone, nitro, oxadiazole, oxazine, perilone, perinone, perylene, phenazine, phenothiazine, phthalocyanin, polyene/carotenoid, porphyrin, pyranthrone, pyrazolanthrone, pyrazolone, pyrimidinoanthrone, pyronine, quinacridone, quinoline, quinophthalone, squarane, stilbene, styryl, tetrazolium, thiazine, thioindigo, thiopyronine, triarylmethane and xanthene dyes.

If they are present, the content of direct dye(s) in the composition generally ranges from 0.001 to 20% by weight relative to the dye composition, and preferably from 0.01 to 10% of the total weight of the dye composition.

As regards the oxidation bases, they can be chosen in particular from o-phenylenediamines, p-phenylenediamines, bisphenylalkylenediamines, o-aminophenols, p-aminophenols, bis-p-aminophenols, heterocyclic bases, their addition salts with an acid or a base, and also mixtures thereof.

In general, when they are present in the composition, the content of oxidation base(s) represents from 0.0005 to 12% by weight relative to the weight of the dye composition, advantageously from 0.005 to 8% by weight relative to the weight of the dye composition.

As regards the couplers optionally combined with the abovementioned oxidation bases, use may be made of one or more compounds chosen from m-aminophenols, m-phenylenediamines, m-diphenols, naphthols, heterocyclic couplers, their addition salts with an acid, and also mixtures thereof.

When they are present, these couplers represent more especially from 0.0001 to 10% by weight relative to the weight of the dye composition, and preferably from 0.005 to 5% by weight relative to the weight of the dye composition.

In general, the addition salts with an acid or with a base, of the oxidation bases and couplers, are in particular chosen from addition salts with hydrochloric acid, hydrobromic acid, sulphuric acid, tartaric acid, lactic acid and acetic acid, and addition salts with sodium hydroxide, potassium hydroxide, aqueous ammonia, amines and alkanolamines.

The composition according to the invention may also comprise at least one surfactant, preferably nonionic, anionic, amphoteric or zwitterionic.

Among the nonionic surfactants, mention may be made of alcohols, alpha-diols, and polyethoxylated and/or polypropoxylated alkylphenols having a hydrocarbon chain comprising, for example, from 8 to 30 carbon atoms, preferably from 8 to 18 carbon atoms, it being possible for the number of ethylene oxide and/or propylene oxide groups to range in particular from 2 to 50.

Mention may also be made of copolymers of ethylene oxide and of propylene, condensates of ethylene oxide and/or of propylene with fatty alcohols; polyethoxylated fatty amides preferably having from 2 to 30 mol of ethylene oxide; polyethoxylated fatty amines preferably having from 2 to 30 mol of ethylene oxide; oxyethylenated sorbitan fatty acid esters having from 2 to 30 mol of ethylene oxide; sucrose fatty acid esters, polyethylene glycol fatty acid esters, alkylpolyglycosides, N-alkylglucamine derivatives, etc.

Among the anionic surfactants, mention may be made, inter alia, of salts (in particular alkali metal salts, especially sodium or magnesium salts, ammonium salts, amine salts or amino alcohol salts) of alkyl sulphates, alkyl ether sulphates, alkylamidoether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates, $(C_6-C_{24})$alkyl sulphosuccinates, $(C_6-C_{24})$alkyl ether sulphosuccinates, $(C_6-C_{24})$alkylamide sulphosuccinates, $(C_6-C_{24})$alkyl sulphoacetates, $(C_6-C_{24})$acyl sarcosinates and glutamates, carboxylic esters of $(C_6-C_{24})$alkylpolyglycosides, alkyl sulphosuccinamates, acyl isothionates and N-acyltaurates, the alkyl or acyl radical of all these various compounds preferably containing from 12 to 20 carbon atoms, and the aryl radical preferably denoting a phenyl or benzyl group.

Also suitable are fatty acid salts such as salts of oleic acid, ricinoleic acid, palmitic acid and stearic acid, hydrogenated coconut oil acid or non-hydrogenated coconut oil acid; alkyl-D-galactoside uronic acids and their salts, polyoxyalkylenated carboxylic $(C_6-C_{24})$alkyl ether acids, polyoxyalkylenated carboxylic $(C_6-C_{24})$alkyl aryl ether acids, polyoxyalkylenated carboxylic $(C_6-C_{24})$alkylamido ether acids, and their salts, in particular those containing from 2 to 50 alkylene oxide, in particular ethylene oxide, groups, and mixtures thereof.

As regards the amphoteric or zwitterionic surfactants, those which are particularly suitable are aliphatic secondary or tertiary amine derivatives in which the aliphatic radical is a linear or branched chain containing 8 to 18 carbon atoms and containing at least one water-solubilizing anionic group (for example carboxylate, sulphonate, sulphate, phosphate or phosphonate); mention may also be made of $(C_8-C_{20})$ alkylbetaines, sulphobetaines, $(C_8-C_{20})$alkylamido$(C_1-C_6)$ alkylbetaines or $(C_8-C_{20})$alkylamido$(C_1-C_6)$alkylsulphobetaines.

Among the amine derivatives, mention may be made of amphocarboxyglycinates and amphocarboxypropionates, such as, for example, disodium cocoamphodiacetate, disodium lauroamphodiacetate, disodium caprylamphodiacetate, disodium cocoamphodipropionate, disodium lauroamphodipropionate, etc. (products of the Miranol® range, in particular Miranol® C2M concentrate, sold by the company Rhodia Chimie).

The content of surfactant in the composition usually represents from 0.01 to 40% by weight, and preferably from 0.5 to 30% by weight, of the total weight of the composition.

The dye composition in accordance with the invention may also comprise various conventionally used adjuvants, such as anionic, cationic, nonionic, amphoteric or zwitterionic polymers, mineral thickeners, antioxidants, penetrating agents, fragrances, buffers, dispersing agents, conditioning agents such as, for example, cations, modified or unmodified, volatile or nonvolatile silicones, cationic amphiphilic polymers, film-forming agents, ceramides, vitamins or provitamins, preserving agents, stabilizers, opacifiers or matting agents such as titanium dioxide, mineral fillers, such as clays, silicas, in particular fumed silicas of hydrophilic or hydrophobic nature, sunscreens, etc.

The adjuvants mentioned above are generally present in an amount, for each of them, of between 0.01 and 20% by weight relative to the weight of the composition.

The medium of the dye composition is a cosmetically acceptable medium.

It preferably consists of an aqueous medium comprising water and, optionally, one or more cosmetically acceptable organic solvents. More particularly, the solvents are chosen from linear or branched, preferably saturated, monoalcohols or diols comprising 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol or phenylethyl alcohol; glycols or glycol ethers such as, for example, ethylene glycol monomethyl ether, monoethyl ether and monobutyl ether, propylene glycol or ethers thereof such as, for example, propylene glycol monomethyl ether, butylene glycol, dipropylene glycol; and also diethylene glycol alkyl ethers, in particular of $C_1-C_4$, such as, for example, diethylene glycol monoethyl ether or monobutyl ether, alone or as a mixture.

When they are present, the usual solvent(s) described above normally represent(s) from 1 to 40% by weight, more preferably from 5 to 30% by weight, relative to the total weight of the dye composition.

The composition according to the invention may also comprise at least one oxidizing agent.

Usually, the oxidizing agent is chosen from hydrogen peroxide, alkali metal peroxides or alkaline-earth metal peroxides, for instance sodium peroxide, potassium peroxide or magnesium peroxide; urea peroxide, alkali metal bromates or alkali metal ferricyanides; enzymes such as, for example, peroxidases or two-electron or four-electron oxidoreductases, alone or as mixtures.

If it is present, the content of oxidizing agent in the dye composition according to the invention is generally between 1 and 20% by weight relative to the weight of the dye composition, preferably between 1 and 12% by weight relative to the weight of the dye composition.

It should be noted that this variant is suitable when it is desired to observe, in addition to the dyeing effect obtained, inter alia, by the direct dye according to the invention, a lightening effect on the fibers.

This same variant is, in addition, implemented when the dye composition according to the invention comprises at least one oxidation base and, optionally, a coupler.

The pH of the dye composition according to the invention is generally between approximately 3 and 12, and preferably between approximately 5 and 11.

It can be adjusted to the desired value by means of acidifying or basifying agents.

Among the acidifying agents, mention may be made, by way of examples, of mineral or organic acids such as hydrochloric acid, orthophosphoric acid, sulphuric acid or acetic acid.

Among the basifying agents, mention may be made, by way of examples, of aqueous ammonia, alkaline carbonates, alkanolamines such as monoethanolamine, diethanolamine and triethanolamine and also derivatives thereof, sodium hydroxide, potassium hydroxide and the compounds of formula (A) below:

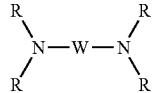

in which W is a propylene residue optionally substituted with a hydroxyl group or a $C_1$–$C_6$ alkyl radical; the radicals R, which may be identical or different, represent a hydrogen atom, a $C_1$–$C_6$ alkyl radical or a $C_1$–$C_6$ hydroxyalkyl radical.

It should be noted that the composition may be in the form of a thickened or non-thickened lotion, a cream, a gel, a foam or a spray, or any other form suitable for the subsequent application of this composition.

A process for dyeing human keratin fibers, in particular such as the hair, using the composition according to the invention, will now be described.

Thus, the following steps may be carried out:
a) said fibers, dry or wet, are brought into contact with the dye composition according to the invention for a period of time sufficient to develop the coloration,
b) the fibers are optionally rinsed,
c) the fibers are optionally washed and rinsed,
d) the fibers are dried or are left to dry.

When the dye composition comprises at least one oxidizing agent, the composition applied to the fibers in step a) is preferably obtained by extemporaneous mixing of the composition according to the invention, without oxidizing agent, with a composition comprising at least said oxidizing agent.

This oxidizing agent is preferably hydrogen peroxide.

Advantageously, the oxidizing composition is of the type of those conventionally used in the dyeing field.

The composition thus obtained is therefore applied to the wet or dry keratin fibers and then left on the fibers for a period of time sufficient to obtain the desired coloration.

The application time is generally approximately 5 to 60 minutes, and more particularly approximately 5 to 40 minutes.

The temperature required to develop the coloration is generally between ambient temperature (15 to 25° C.) and 80° C. and more particularly between 15 and 40° C.

Once this step has been carried out, the fibers are optionally rinsed, are optionally washed with a shampoo, and are rinsed. The fibers are then dried or are left to dry.

Finally, a subject of the present invention is a multicompartment device in which a first compartment contains a dye composition comprising at least one cationic triazo dye of formula (I) described above, and a second compartment contains an oxidizing agent.

Concrete but nonlimiting examples of the invention will now be presented.

EXAMPLE 1

Syntheses

1/ Synthesis of a Compound of Formula (I) Below:

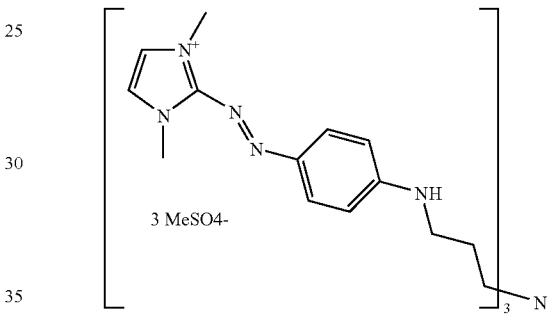

General reaction scheme:

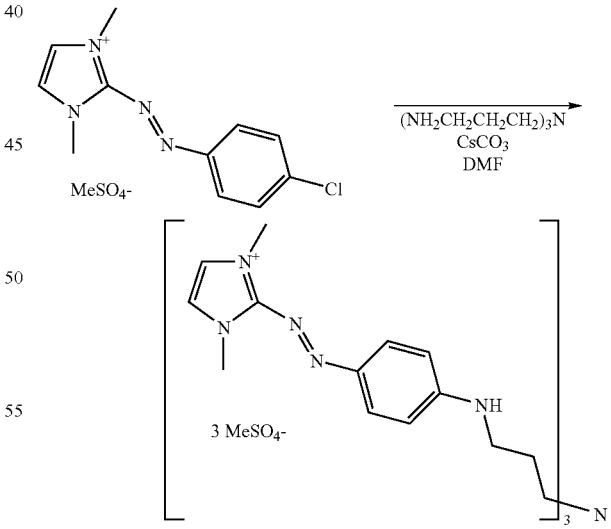

Synthesis:
4.68 g of 2-[(4-chlorophenyl)diazenyl]-1,3-dimethyl-1H-imidazol-3-ium methosulphate are dissolved in 50 ml of dimethylformamide.

5 g of cesium carbonate are then added, followed by 0.5 g of tris(3-aminopropyl)amine.

The mixture obtained is conserved with stirring at 80° C. for 2 hours and then a further 0.5 g of tris(3-aminopropyl)amine is added.

0.5 g of tris(3-aminopropyl)amine is added after 16 hours with stirring at 80° C., and the mixture is left under these temperature conditions and with stirring for 4 hours.

The resulting solution is then cooled to ambient temperature and filtered, and then the solvent is evaporated off so as to obtain a red-coloured oily compound.

The product is then purified on an HPLC column.

The analyses confirm the above structure of the compound obtained.

2/ Synthesis of the Comparative Compound of Formula below:

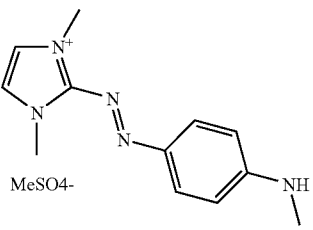

MeSO4-

General reaction scheme:

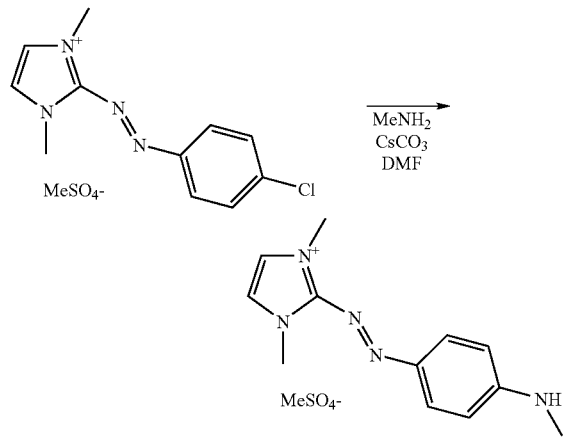

Synthesis:

1 g of 2-[(4-chlorophenyl)diazenyl]-1,3-dimethyl-1H-imidazol-3-ium methosulphate is dissolved in 50 ml of 2-propanol, and then 2 g of methylamine are added.

The mixture is kept at reflux, with stirring, for 4 hours and then cooled to ambient temperature and filtered.

The solvent is evaporated off so as to obtain a red solid.

The product is then purified on a column (liquid chromatography; silica; eluent; methanol/dichloromethane).

The analyses confirm the above structure of the compound obtained.

EXAMPLE 2

Application

1/ Dyeing

A solution buffered at pH 9 is prepared by mixing 2 g of ammonium acetate in 40 ml of water. The pH is adjusted by adding aqueous ammonia and the volume is made up to 100 ml by adding deionized water.

$5 \times 10^{-4}$ mol % of each of the dyes obtained in Example 1 above are dissolved in the abovementioned buffered solution.

A lock of white hair is placed in contact with the resulting solution, with a bath ratio of 10 to 1.

After 20 minutes of application, the lock is rinsed with deionized water in order to remove the excess dye solution.

A lock of red hair is obtained for each of the two dyes.

2/ Shampoo Test

Each lock of hair dyed according to the preceding step is hand-washed with a solution comprising 1% by volume of shampoo, for 30 seconds, and then rinsed with 200 ml of water.

The process is repeated 6 times.

3/ Results

The locks obtained in the two cases kept the same colour, but the intensity of the colour of the lock dyed with the compound in accordance with the invention is visually greater than that of the lock dyed with a compound that does not fall within the context of the invention. This shows, consequently, that the dye composition according to the invention makes it possible to obtain colorations that are more resistant to shampooing.

EXAMPLE 3

Synthesis

Synthesis of a Compound of Formula Below:

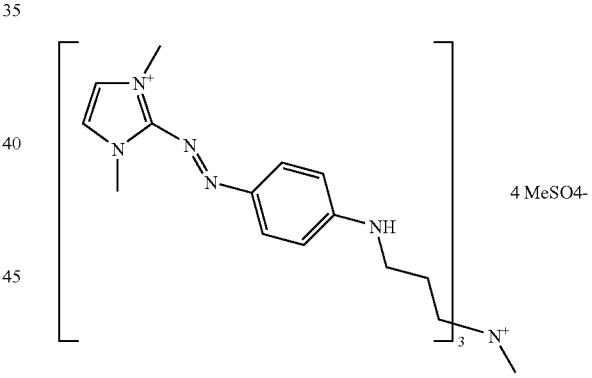

4 MeSO4-

General reaction scheme:

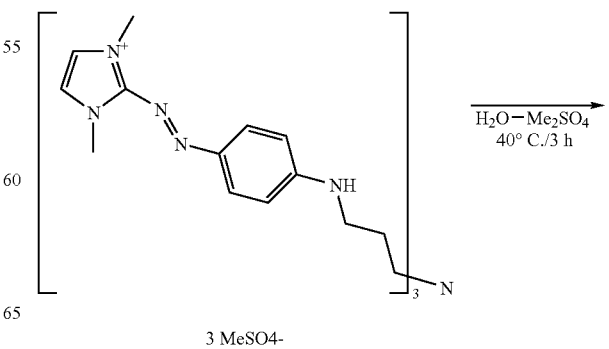

$\xrightarrow{H_2O-Me_2SO_4}$
40° C./3 h

3 MeSO4-

-continued

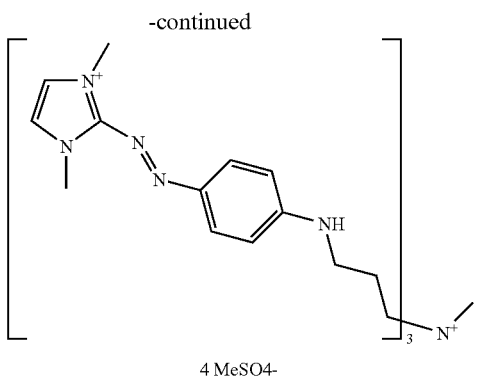

4 MeSO4-

Synthesis:

0.5 g of the tricationic dye obtained in Example 1-1 is dissolved in 50 ml of water.

1 equivalent of dimethyl sulphate is then added.

The mixture obtained is conserved at 40° C. with stirring for 3 hours.

The resulting solution is poured into 300 ml of acetone. The precipitate is filtered off and washed with 500 ml of acetone so as to obtain the tetra-cationic dye in the form of a red-coloured powder.

The analyses confirm the above structure of the compound obtained.

A lock is dyed in accordance with the description given in Example 2.

A red-coloured lock is obtained.

EXAMPLE 4

Synthesis

Synthesis of a Compound of Formula Below:

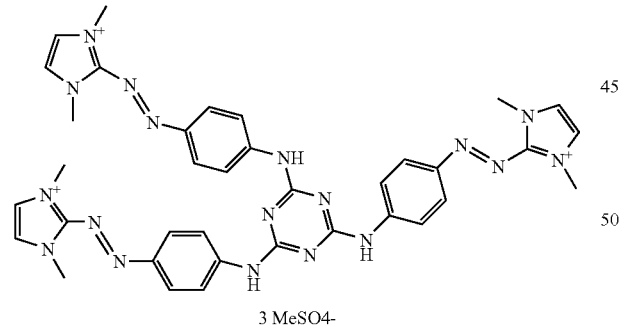

3 MeSO4-

General reaction scheme:

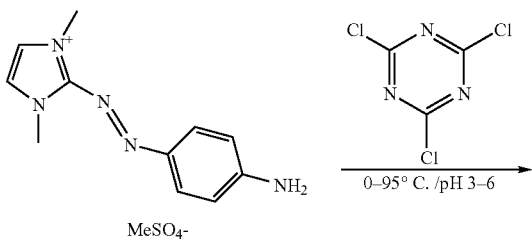

-continued

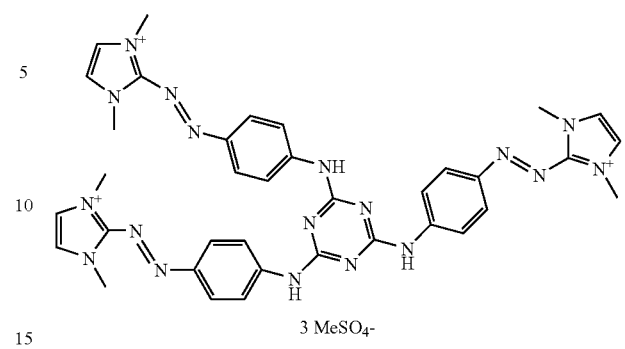

3 MeSO4-

Synthesis:

0.5 g of the monocationic monoazo dye is dissolved in 20 ml of water.

0.33 equivalent of trichlorotriazine is dissolved in 10 ml of acetone. The solution containing the trichlorotriazine is poured into a mixture of ice (10 g) and water (50 ml).

The solution containing the monocationic dye is then added.

The mixture obtained is conserved at 0–5° C. with stirring for 30 minutes.

The reaction mixture is subsequently stirred at 40° C. for 30 minutes and then at 95° C. for 2 hours.

During the reaction, a saturated aqueous $NaHCO_3$ solution is added dropwise so as to maintain the pH between 3 and 6.

The resulting solution is cooled to ambient temperature and poured into 300 ml of acetone. The precipitate is filtered off and then washed with 500 ml of acetone (500 ml) so as to obtain the red-coloured tricationic dye.

The analyses confirmed the above structure of the compound obtained.

A lock is dyed in accordance with the description given in Example 2.

A red-coloured lock is obtained.

The invention claimed is:

1. A cationic direct dye of formula (I):

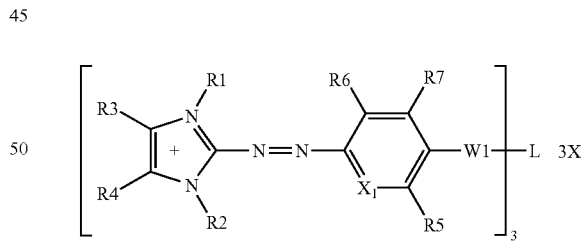

wherein:

$W_1$ is chosen from $-NR_8-$ and $-O-$;

$X_1$ is chosen from N and $CR_9$;

$R_1$ and $R_2$, which may be identical or different, are each a hydrocarbon chain;

$R_3$ and $R_4$, which may be identical or different, are each chosen from hydrogen atoms, halogen atoms, nitro groups, cyano groups, and hydrocarbon chains;

$R_5$, $R_6$, $R_7$, $R_8$ and $R_9$, which may be identical or different, are each chosen from hydrogen atoms and hydrocarbon chains;

L is chosen from:

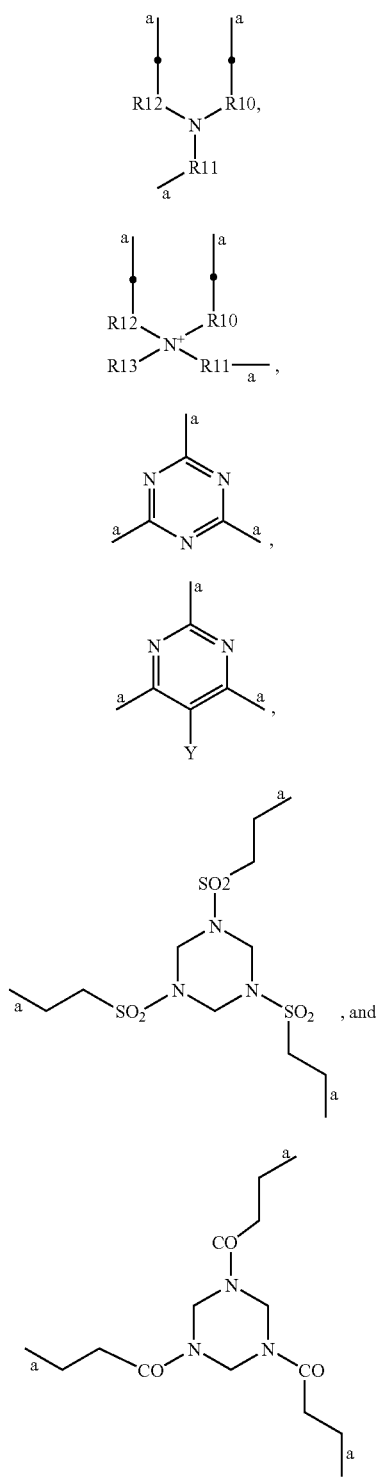

wherein:
$R_{10}$, $R_{11}$, $R_{12}$ and $R_{13}$, which may be identical or different, are each a hydrocarbon chain;
Y is a halogen atom;
the bond a in formulas (II), (III), (IV), (V), (VI), and (VII) is connected to group $W_1$ of formula (I); and X is chosen from cosmetically acceptable organic anions and cosmetically acceptable mineral anions.

2. The direct dye according to claim 1, wherein the hydrocarbon chains in formulas (I), (II), (III), (IV), (V), (VI), and (VII) are chosen from:
linear and branched, saturated and unsaturated $C_1$–$C_8$ hydrocarbon chains optionally interrupted with at least one heteroatom and optionally interrupted with at least one group chosen from carbonyl and $SO_2$ groups, wherein the chains do not comprise a first heteroatom adjacent to a second heteroatom, and further do not comprise a first carbonyl or $SO_2$ group adjacent to a second carbonyl or $SO_2$ group; and
hydrocarbon chains which form aromatic $C_5$–$C_6$ groups;
and wherein the hydrocarbon chains are optionally substituted with at least one radical chosen from hydroxyl radicals, halogen atoms, $C_1$–$C_4$ alkoxy radicals; monohydroxyalkoxy radicals wherein the alkyl portion is chosen from linear and branched, substituted and unsubstituted $C_1$–$C_4$ alkyl radicals; polyhydroxyalkoxy radicals, wherein the alkyl portion is chosen from linear and branched, substituted and unsubstituted $C_2$–$C_4$ alkyl radicals; amino radicals optionally substituted with at least one radical chosen from linear and branched, substituted and unsubstituted $C_1$–$C_4$ alkyl radicals that may be identical or different; thiol radicals; alkylthio radicals wherein the alkyl portion is chosen from linear and branched, substituted and unsubstituted $C_1$–$C_4$ alkyl radicals; carboxyl radicals in acid form; carboxyl radicals in salified form with an alkali metal or an optionally substituted ammonium; alkoxycarbonyl radicals wherein the alkyl portion is chosen from linear and branched, substituted and unsubstituted $C_1$–$C_4$ alkyl radicals; alkylamide radicals wherein the alkyl portion is chosen from linear and branched, substituted and unsubstituted $C_1$–$C_4$ alkyl radicals; alkylcarbamyl radicals wherein the alkyl portion is chosen from linear and branched, substituted and unsubstituted $C_1$–$C_4$ alkyl radicals; nitro radicals; sulphonyl radicals; alkylsulphonyl radicals wherein the alkyl portion is chosen from linear and branched, substituted and unsubstituted $C_1$–$C_4$ alkyl radicals; sulphonylamino radicals; and alkylsulphonylamido radicals wherein the alkyl portion is chosen from linear and branched, substituted and unsubstituted $C_1$–$C_4$ alkyl radicals.

3. The direct dye according to claim 1, wherein $R_1$ and $R_2$, which may be identical or different, are each chosen from $C_1$–$C_8$ alkyl and $C_2$–$C_8$ alkenyl radicals optionally substituted with at least one radical chosen from hydroxyl; amino; amino substituted with at least one $C_1$–$C_8$ alkyl radical optionally substituted with at least one hydroxyl radical; $C_1$–$C_8$ alkoxy radicals, and $C_6$-aryl ($C_1$–$C_4$) alkyl radicals.

4. The direct dye according to claim 3, wherein $R_1$ and $R_2$, which may be identical or different, are each chosen from $C_1$–$C_4$ alkyl radicals and benzyl radicals.

5. The direct dye according to claim 4, wherein $R_1$ and $R_2$ which may be identical or different, are each chosen from methyl and ethyl radicals.

6. The direct dye according to claim 1, wherein $R_3$ and $R_4$, which may be identical or different, are each chosen from hydrogen atoms, halogen atoms, nitro groups, cyano groups, $C_1$–$C_8$ alkyl and $C_2$–$C_8$ alkenyl radicals optionally substituted with at least one radical chosen from hydroxyl; amino; amino substituted with at least one $C_1$–$C_8$ alkyl radical optionally substituted with at least one hydroxyl radical;

19

$C_1$–$C_8$ alkoxy radicals, $C_1$–$C_8$ alkylthio radicals, sulphonylamino radicals, and phenyl radicals.

7. The direct dye according to claim 6, wherein $R_3$ and $R_4$, which may be identical or different, are each chosen from hydrogen atoms, chlorine atoms, $C_1$–$C_8$ alkyl and $C_2$–$C_8$ alkenyl radicals optionally substituted with at least one radical chosen from hydroxyl; amino; amino substituted with at least one $C_1$–$C_8$ alkyl radical optionally substituted with at least one hydroxyl radical; $C_1$–$C_8$ alkoxy radicals, and phenyl radicals.

8. The direct dye according to claim 7, wherein $R_3$ and $R_4$, which may be identical or different, are each chosen from hydrogen atoms, chlorine atoms, and phenyl radicals.

9. The direct dye according to claim 1, wherein $R_5$, $R_6$, $R_7$, $R_8$ and $R_9$, which may be identical or different, are each chosen from hydrogen atoms; $C_1$–$C_8$ alkyl and $C_2$–$C_8$ alkenyl radicals optionally substituted with at least one radical chosen from hydroxyl; amino; amino substituted with at least one $C_1$–$C_8$ alkyl radical optionally substituted with at least one hydroxyl radical; $C_1$–$C_8$ alkoxy radicals; $C_1$–$C_8$ alkylthio radicals; and sulphonylamino radicals.

10. The direct dye according to claim 9, wherein $R_5$, $R_6$, $R_7$, $R_8$ and $R_9$, which may be identical or different, are each chosen from hydrogen atoms, $C_1$–$C_4$ alkyl radicals optionally substituted with at least one radical chosen from hydroxyl; amino; amino substituted with at least one $C_1$–$C_8$ alkyl radical optionally substituted with at least one hydroxyl radical; and $C_1$–$C_4$ alkoxy radicals.

11. The direct dye according to claim 10, wherein $R_5$, $R_6$, $R_7$, $R_8$ and $R_9$, which may be identical or different, are each chosen from hydrogen atoms and $C_1$–$C_4$ alkyl radicals.

12. The direct dye according to claim 1, wherein $R_3$, $R_4$, $R_5$, $R_6$, $R_7$, $R_8$ and $R_9$ are each a hydrogen atom.

13. The direct dye according to claim 1, wherein $R_{10}$, $R_{11}$, $R_{12}$ and $R_{13}$, which may be identical or different, are each chosen from hydrogen atoms; $C_1$–$C_8$ alkyl and $C_2$–$C_8$ alkenyl radicals optionally substituted with at least one radical chosen from hydroxyl; amino; amino substituted with at least one $C_1$–$C_8$ alkyl radical optionally substituted by at least one hydroxyl radical; $C_1$–$C_8$ alkoxy radicals; $C_1$–$C_8$ alkylthio radicals; and sulphonylamino radicals.

14. The direct dye according to claim 13, wherein the radicals $R_{10}$, $R_{11}$, $R_{12}$ and $R_{13}$, which may be identical or different, are each chosen from $C_1$–$C_4$ alkoxy and $C_1$–$C_4$ alkyl radicals optionally substituted with at least one radical chosen from hydroxyl; amino; and amino substituted with at least one $C_1$–$C_4$ alkyl radical optionally substituted with at least one hydroxyl radical.

15. The direct dye according to claim 14, wherein $R_{10}$, $R_{11}$, $R_{12}$ and $R_{13}$, which may be identical or different, are each chosen from ethyl, n-propyl, and n-butyl radicals.

16. The direct dye according to claim 1, wherein $X_1$ is —$CR_9$—.

17. The direct dye according to claim 16, wherein $R_9$ is hydrogen.

18. The direct dye according to claim 1, wherein $W_1$ is —$NR_8$—.

19. The direct dye according to claim 18, wherein $R_8$ is chosen from $C_1$–$C_4$ alkyl and hydrogen.

20. The direct dye according to claim 1, wherein X is chosen from mineral anions chosen from halides, hydroxides, sulphates, hydrogen sulphates; organic anions chosen from acetate, citrate, tartrate, alkyl suiphates wherein the alkyl portion is chosen from linear and branched $C_1$–$C_6$ alkyl, alkylsulphonates wherein the alkyl portion is chosen from linear and branched $C_1$–$C_6$ alkyl radicals, arylsulphonates wherein the aryl portion is optionally substituted with at least one $C_1$–$C_4$ alkyl radical.

21. The direct dye according to claim 1, further comprising an additional cosmetically acceptable anion chosen from organic and mineral anions.

22. The direct dye of claim 21, wherein said direct dye is chosen from:

2-((E)-{4-[(3-{bis[3-({4-[(E)-(1,3-dimethyl-1H-imidazol-3-ium-2-yl)diazenyl]phenyl}amino)-propyl]amino}propyl)amino]phenyl}diazenyl)-1,3-dimethyl-1H-imidazol-3-ium trichloride;

2-{(E)-[4-({3-[bis[3-({4-[(E)-(1,3-dimethyl-1H-imidazol-3-ium-2-yl)diazenyl]phenyl}amino)-propyl](methyl)ammonio]propyl}amino)phenyl]-diazenyl}-1,3-dimethyl-1H-imidazol-3-ium tetrachloride;

2-((E)-{4-[{3-[bis{3-[{4-[(E)-(1,3-dimethyl-1H-imidazol-3-ium-2-yl)diazenyl]phenyl}(methyl)-amino)propyl}(methyl)ammonio]propyl}(methyl)-amino]phenyl}diazenyl) -1,3-dimethyl-1H-imidazol-3-ium tetrachloride;

2-(E)-{4-[{3-[bis{3-[{4-[(E)-(1,3-diethyl-1H-imidazol-3-ium-2-yl)diazenyl]phenyl}(ethyl)-amino]propyl}(ethyl)ammonio]propyl}(ethyl)-amino]phenyl}diazenyl)-1,3-diethyl-1H-imidazol-3-ium tetrachloride;

2-((E)-{4-[(3-bis{3-[{4-[(E)-(1,3-dimethyl-1H-imidazol-3-ium-2-yl)diazenyl]phenyl}(ethyl)-amino]propyl}(ethyl)ammonio]propyl}(ethyl) -amino]phenyl}diazenyl)-1,3-dimethyl-1H-imidazol-3-ium tetrachloride;

2-((E)-{4-[(3-{3,5-bis[3-({4-[(E)-(1,3-dimethyl-1H-imidazol-3-ium-2-yl)diazenyl]phenyl}amino)-propanoyl]-1,3,5-triazinan-1-yl}-3-oxopropyl]amino]phenyl}diazenyl)-1,3-dimethyl-1H-imidazol-3-ium trichloride;

2-((E)-{4-[[3-(3,5-bis{3-[{4-[(E)-(1,3-dimethyl-1H-imidazol-3-ium-2-yl)diazenyl]phenyl}(ethyl)-amino]propanoyl)-1,3,5-triazinan-1-yl)-3-oxo-propyl](ethyl) amino]phenyl}diazenyl)-1,3-dimethyl-1H-imidazol-3-ium trichloride;

2-{(E)-[4-({2-[(3,5-bis{[2-[{4-[(E)-(1,3-dimethyl-1H-imidazol-3-ium-2-yl) diazenyl]phenyl}-amino)ethyl]sulphonyl}-1,3,5-triazinan-1-yl) sulphonyl]ethyl}amino)phenyl]diazenyl}-1,3-dimethyl-1H-imidazol-3-ium trichloride;

2-((E)-{4-[(2-{[3,5-bis({2-[{4-[(E)-(1,3-dimethyl-1H-imidazol-3-ium-2-yl)diazenyl]phenyl}-(ethyl)amino]ethyl}sulphonyl)-1,3,5-triazinan-1-yl]sulphonyl}ethyl)(ethyl)amino]phenyl}-diazenyl)-1,3-dimethyl-1H-imidazol-3-ium trichloride;

2-[(E)-(4-{[4,6-bis({4-[(E)-(1,3-dimethyl-1H-imidazol-3-ium-2-yl)diazenyl]phenyl}amino)-1,3,5-triazin-2-yl]amino}phenyl)diazenyl]-1,3-dimethyl-1H-imidazol-3-ium trichloride;

2-((E)-{4-[(4,6-bis[{4-[(E)-(1,3-dimethyl-1H-imidazol-3-ium-2-yl)diazenyl]phenyl}(methyl)-amino)-1,3,5-triazin-2-yl](methyl)amino]-phenyl}diazenyl)) -1,3-dimethyl-1H-imidazol-3-ium trichloride;

[2-[(E)-(4-{[5-chloro-2,6-bis({4-[(E)-(1,3-dimethyl-1H-imidazol-3-ium-2-yl) diazenyl]phenyl)-amino)pyrimidin-4-yl]amino}phenyl)diazenyl]-1,3-dimethyl-1H-imidazol-3-ium trichloride;

2-((E)-{4-[{5-chloro-2,6-bis({4-[(E)-(1,3-dimethyl-1H-imidazol-3-ium-2-yl) diazenyl]phenyl}-(methyl)amino]pyrimidin-4-yl}(methyl)amino]-phenyl}diazenyl)-1,3-dimethyl-1H-imidazol-3-ium trichloride; and compounds wherein the counterion is different from chlorine and is chosen from cosmetically acceptable organic anions and cosmetically acceptable mineral anions.

23. A dye composition comprising, in a medium suitable for dyeing human keratin fibers, at least one cationic direct dye of formula (I):

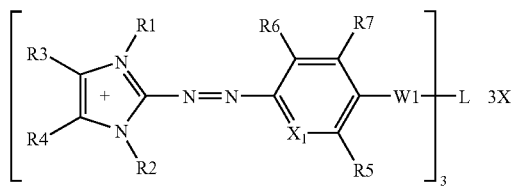

wherein:

$W_1$ is chosen from —$NR_8$— and —O—;

$X_1$ is chosen from N and $CR_9$;

$R_1$ and $R_2$, which may be identical or different, are each a hydrocarbon chain;

$R_3$ and $R_4$, which may be identical or different, are each chosen from hydrogen atoms, halogen atoms, nitro groups, cyano groups, and hydrocarbon chains;

$R_5$, $R_6$, $R_7$, $R_8$ and $R_9$, which may be identical or different, are each chosen from hydrogen atoms and hydrocarbon chains;

L is chosen from:

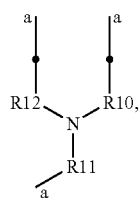
Formula (II)

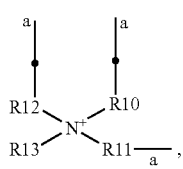
Formula (III)

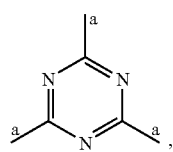
Formula (IV)

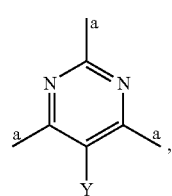
Formula (V)

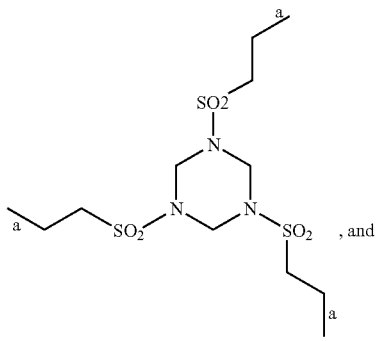
Formula (VI)

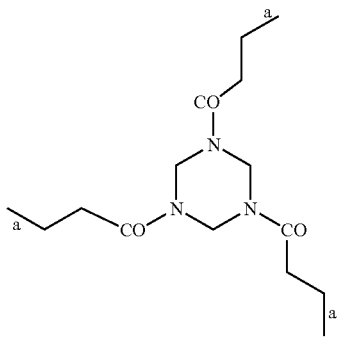
Formula (VII)

wherein:

$R_{10}$, $R_{11}$, $R_{12}$ and $R_{13}$, which may be identical or different, are each a hydrocarbon chain;

Y is a halogen atom;

the bond a in formulas (II), (III), (IV), (V), (VI), and (VII) is connected to group $W_1$ of formula (I); and X is chosen from cosmetically acceptable organic anions and cosmetically acceptable mineral anions.

24. The dye composition according to claim 23, wherein the amount of the at least one cationic dye ranges from 0.001 to 20% by weight relative to the total weight of the dye composition.

25. The dye composition according to claim 24, wherein the amount of the at least one cationic dye ranges from 0.01 to 10% by weight relative to the total weight of the dye composition.

26. The dye composition according to claim 23, further comprising at least one direct dye different from the direct dye of formula (I) and chosen from cationic, anionic, and nonionic dyes, in an amount ranging from 0.001 to 20% by weight relative to the total weight of the dye composition.

27. The dye composition according to claim 26, wherein the amount of the at least one direct dye different from the direct dye of formula (I) ranges from 0.01 to 10% by weight relative to of the total weight of the dye composition.

28. The dye composition according to claim 23, further comprising at least one oxidation base in an amount ranging from 0.0005 to 12% by weight relative to the total weight of the dye composition.

29. The dye composition according to claim 28, wherein the amount of the at least one oxidation base ranges from 0.005 to 8% by weight relative to the total weight of the dye composition.

30. The dye composition according to claim 23, further comprising at least one coupler in an amount ranging from 0.0001 to 10% by weight relative to the total weight of the dye composition.

31. The dye composition according to claim 30, wherein the amount of the at least one coupler ranges from 0.005 to 5% by weight relative to the total weight of the dye composition.

32. The dye composition according to claim 23, further comprising at least one oxidizing agent.

33. The dye composition according to claim 32, wherein the at least one oxidizing agent is chosen from hydrogen peroxide, alkali metal peroxides, alkaline-earth metal peroxides, urea peroxide, alkali metal bromates, alkali metal ferricyanides, enzymes, and mixtures thereof.

34. The dye composition according to claim 32, wherein the amount of the at least oxidizing agent ranges from 1 to 20% by weight relative to the weight of the dye composition.

35. The dye composition according to claim 34, wherein the amount of the at least one oxidizing agent ranges from 1 to 12% by weight relative to the weight of the dye composition.

36. A process for dyeing human keratin fibers, comprising:
bringing the fibers into contact with a dye composition for a period of time sufficient to develop a desired coloration,
optionally rinsing the fibers;
optionally washing and rinsing the fibers; and
drying the fibers or leaving the fibers to dry,
wherein said dye composition comprises, in a medium suitable for dyeing human keratin fibers, at least one cationic direct dye of formula (I):

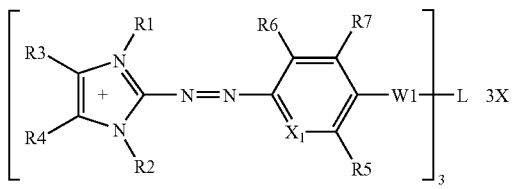

wherein:
$W_1$ is chosen from —$NR_8$— and —O—;
$X_1$ is chosen from N and $CR_9$;
$R_1$ and $R_2$, which may be identical or different, are each a hydrocarbon chain;
$R_3$ and $R_4$, which may be identical or different, are each chosen from hydrogen atoms, halogen atoms, nitro groups, cyano groups, and hydrocarbon chains;
$R_5$, $R_6$, $R_7$, $R_8$ and $R_9$, which may be identical or different, are each chosen from hydrogen atoms and hydrocarbon chains;
L is chosen from:

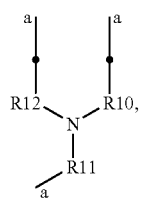

Formula (II)

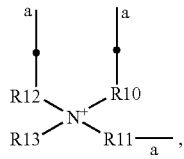

Formula (III)

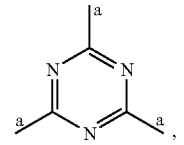

Formula (IV)

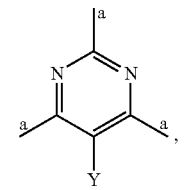

Formula (V)

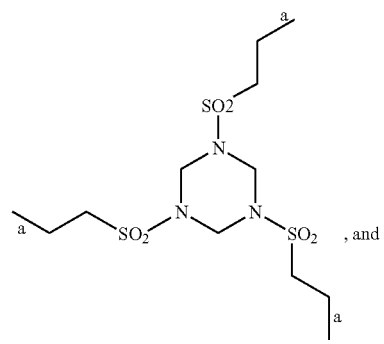

Formula (VI)

, and

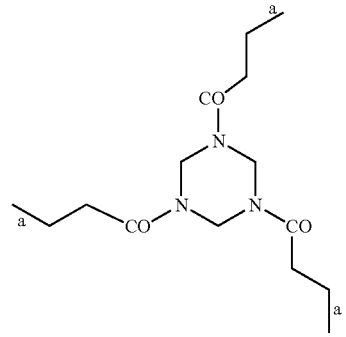

Formula (VII)

wherein:
$R_{10}$, $R_{11}$, $R_{12}$ and $R_{13}$, which may be identical or different, are each a hydrocarbon chain;
Y is a halogen atom;
the bond a in formulas (II), (III), (IV), (V), (VI), and (VII) is connected to group $W_1$ of formula (I); and
X is chosen from cosmetically acceptable organic anions and cosmetically acceptable mineral anions.

37. A multicompartment device for dyeing human keratin fibers, comprising:
at least one first compartment comprising a dye composition, and
at least one second compartment comprising an oxidizing agent, wherein said dye composition comprises, in a medium suitable for dyeing human keratin fibers, at least one cationic direct dye of formula (I):

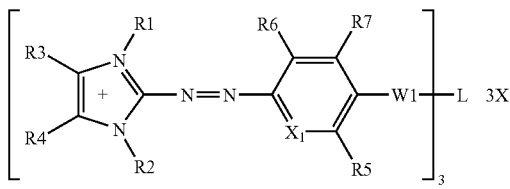

wherein:

$W_1$ is chosen from $-NR_8-$ and $-O-$;

$X_1$ is chosen from N and $CR_9$;

$R_1$ and $R_2$, which may be identical or different, are each a hydrocarbon chain;

$R_3$ and $R_4$, which may be identical or different, are each chosen from hydrogen atoms, halogen atoms, nitro groups, cyano groups, and hydrocarbon chains;

$R_5$, $R_6$, $R_7$, $R_8$ and $R_9$, which may be identical or different, are each chosen from hydrogen atoms and hydrocarbon chains;

L is chosen from:

Formula (II)

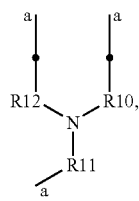

Formula (III)

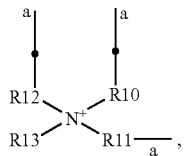

Formula (IV)

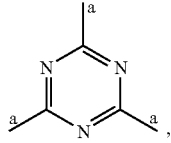

Formula (V)

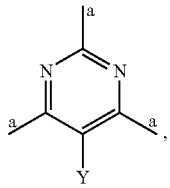

Formula (VI)

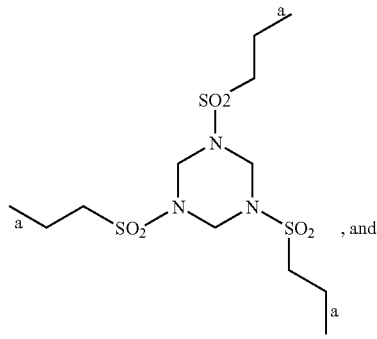

, and

Formula (VII)

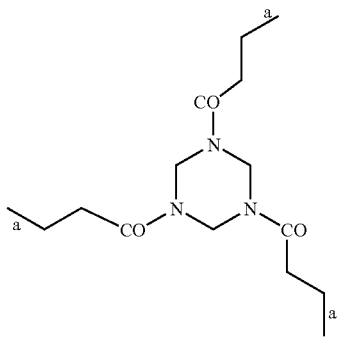

wherein:

$R_{10}$, $R_{11}$, $R_{12}$ and $R_{13}$, which may be identical or different, are each a hydrocarbon chain;

Y is a halogen atom; the bond a in formulas (II), (III), (IV), (V), (VI), and (VII) is connected to group $W_1$ of formula (I); and X is chosen from cosmetically acceptable organic anions and cosmetically acceptable mineral anions.

* * * * *

UNITED STATES PATENT AND TRADEMARK OFFICE
CERTIFICATE OF CORRECTION

| | | |
|---|---|---|
| PATENT NO. | : 7,220,286 B2 | Page 1 of 1 |
| APPLICATION NO. | : 11/033998 | |
| DATED | : May 22, 2007 | |
| INVENTOR(S) | : Andrew Greaves | |

It is certified that error appears in the above-identified patent and that said Letters Patent is hereby corrected as shown below:

In Formula (VI),
at:
claim 1, col. 17, line 37;
claim 23, col. 22, line 7;
claim 36, col. 24, line 27,
"SO2" should read --$SO_2$--.

Signed and Sealed this

Seventh Day of August, 2007

JON W. DUDAS
*Director of the United States Patent and Trademark Office*